United States Patent [19]

Kingsley et al.

[11] 3,995,618
[45] Dec. 7, 1976

[54] CERVICAL TISSUE CELL-GATHERING DEVICE

[75] Inventors: Warren K. Kingsley, Bethlehem, Pa.; Stanley Schoenfeld, Pound Ridge, N.Y.

[73] Assignee: Richardson-Merrell Inc., Wilton, Conn.

[22] Filed: June 16, 1975

[21] Appl. No.: 587,160

[52] U.S. Cl. .................................................. 128/2 B
[51] Int. Cl.² ...................................... A61B 10/00
[58] Field of Search ................................... 128/2 B

[56] References Cited
UNITED STATES PATENTS

| | | | |
|---|---|---|---|
| 2,905,169 | 9/1959 | Nieburgs | 128/2 B |
| 2,955,591 | 10/1960 | MacLean | 128/2 B |
| 3,640,268 | 2/1972 | Davis | 128/2 B |
| 3,800,781 | 4/1974 | Zalucki | 128/2 B |
| 3,877,464 | 4/1975 | Vermes | 128/2 B |

Primary Examiner—Channing L. Pace
Attorney, Agent, or Firm—William J. Stein; Eugene O. Retter; George W. Rauchfuss, Jr.

[57] ABSTRACT

A cervical tissue cell-gathering device is provided which can be self-administered, and which is so arranged as to protect the sample from contamination as it is inserted and withdrawn from the vagina. An improved method for the preparation of Pap smear slides using such a device is described.

6 Claims, 4 Drawing Figures

CERVICAL TISSUE CELL-GATHERING DEVICE

BACKGROUND OF THE INVENTION

Cytologic screening using the Papanicalou test (Pap test) has been used for the past 20 years as an effective means for the early detection of cervical cancer. Although approximately 90 percent of American women are aware of the nature and purpose of the Pap test, about 36 percent of them will not use the test, notwithstanding the fact that symptoms of this cancer can be detected in the very early stages thereby facilitating and making treatment much more effective. The goal of the Uterine Cancer Task Force of the American Cancer Society is to have an annual Pap test for every woman over 20 years of age.

There are two major problems in such a screening of mass populations. The first is the availability of physicians to conduct examinations and conduct the necessary Pap smears. The second problem concerns a reluctance on the part of the female population which is due in part to the time and effort involved in taking the test, the expense — especially for lower socio-economic groups, and lastly, the natural reluctance of many women to have the examination conducted for reasons of modesty.

The Pap test is generally administered by the physician in his office by inserting a speculum into the vagina, thereby exposing the cervix. The surface of the external os is scraped by means of rigid wooden or plastic sticks, and the detritus so obtained is placed upon a glass slide for cytological examination. The use of these probes is traumatic, not infrequently causing injury to the tissues and the risk of subsequent infection. These probes are non-porous in nature and are not capable of gathering or collecting exudates and secretions at the squamocolumnar junction of the uterine cervix which may be useful in indicating the presence of infectious microorganisms such as trichonomads, candida albicans, leptothrix, and other microorganisms of bacterial nature. Since these probes are rigid rather than being soft and flexible, they tend to destroy the friable, cervical cells when smeared against the rigid glass slide. In addition to destroying portions of the sample, the use of a rigid probe tends to smear the specimen non-uniformly onto the slide, making the interpretation of the slide more difficult and reducing he reliability of subsequent tests thereof.

The use of a vaginal irrigation pipette allows a patient to obtain a cell specimen herself. However, the cellular materials obtained in this fashion require a markedly different interpretation as compared to the conventional cervical scrapings obtained via the Pap smear. Additionally, the recovered material is generally suspended in saline solution and must be separated therefrom, requiring an additional step in the diagnostic procedure. Moreover, irrigation of the uterus creates the possibility of flushing abnormal cells into the oviducts thereby contributing to the risk of implantation by seeding.

The present invention describes a cervical tissue cell-gathering device which can be safely used by the individual with a minimum of discomfort and in the privacy of her own home. The nature of this device is such as to create a gentle wiping action in lieu of the scraping action required by the Pap test. By means of this device an untrained individual can obtain a specific cellular sample from the region of the squamocolumnar junction of the cervix, which can then be mailed or transported to the clinic for cytological examination. Moreover, the particular device described herein provides a complete cell representation free from vaginal cell wall contamination and mucous secretions.

PRIOR ART

U.S. Pat. No. 2,847,000 discloses a device for obtaining body cell specimens which incorporates a slide mounted in an open-ended tube. Such specimens, however, are readily contaminated with extraneous vaginal secretions upon insertion and require additional processing for cytological examination.

U.S. Pat. No. 3,776,219 discloses a cervical scraper having a conical polyurethane foam head. This head contains a plurality of petal-like appendages arranged to envelop and protect the head during withdrawal. However, these petals offer no protection against contamination upon insertion and, indeed, are designed to collect a full representation of cells, both endocervical and exocervical for a complete diagnosis of the cervix and vagina.

U.S. Pat. No. 3,857,384 discloses a cervical tissue cell specimen-gathering device in which the cell sampler is a rotatable slide carrier adapted to contain a microscopic slide. The principal feature of this invention is an outer insertion tube through which the slide carrier is slidably and rotatably inserted.

While these devices are all useful, they are not entirely satisfactory. Little, if any, protection is afforded to the cell-gathering means upon entry into the vagina from the normal vaginal secretions which are present. Thus, there is a need for a cervical tissue cell-gathering device which provides for a more complete cervical tissue representation free from vaginal secretions and contamination.

SUMMARY OF THE INVENTION

Accordingly, the present invention comprises an economical, highly efficient, self-administered, tissue cell-gathering device whereby a woman can collect cervical tissue for cytological evaluation without pain and without serious trauma to tissue at the sampling site and be able to do so at her own leisure and privacy. This invention describes such a device which provides for a highly specific cervical test sampling and which is essentially free of contamination from vaginal secretions.

In a more limited aspect of this invention there is described a self-administered method for the collection of cells from the region of the squamocolumnar junction of the uterine cervix and their protection in transportation or mailing to clinical laboratories for subsequent cytological examination.

In a still more limited aspect of this invention there is described a method of preparing Pap smear slides which enables a reliable and accurate diagnosis by the physician in the detection of cervical carcinoma.

Other advantages of this invention will become apparent by reference to the following specification and accompanying drawing.

DETAILED DESCRIPTION OF THE INVENTION

Figure 1:
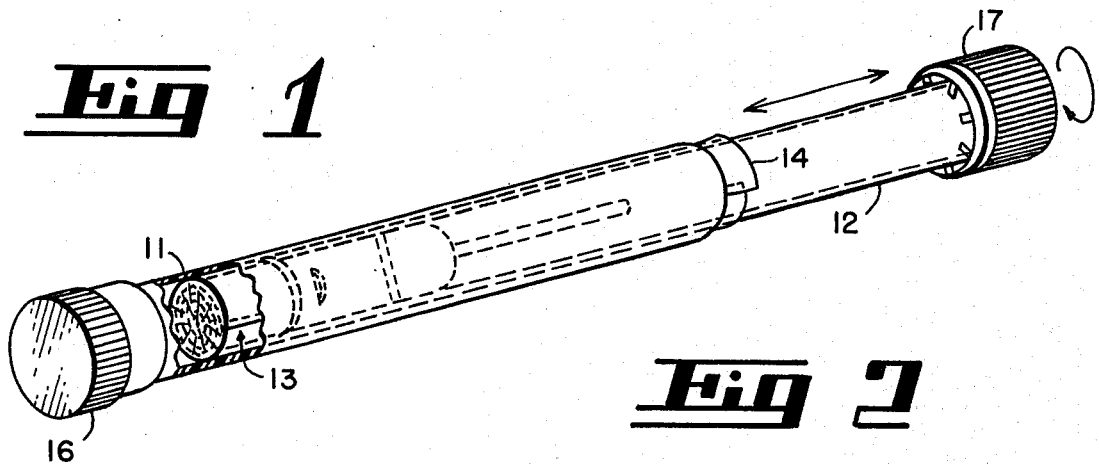
FIG. 1 is a perspective view of a cervical tissue cell-gathering device taken from one side and slightly below at the forward end thereof.

Reference is now made to the accompanying drawing for a better understanding of the nature of the invention. The drawing illustrates the best mode presently contemplated for carrying out the present invention and is not to be construed as a restriction or limitation upon its scope.

As can be seen in FIG. 1, the cervical tissue cell-gathering device is an assembled unit comprising essentially four parts: an outer tube or cylinder 11, an inner tube or plunger 12, a cervical sponge 13 mounted at the leading end of said inner tube which collects the tissue cell specimen, and a thin, flexible mucous sleeve 14, which protects the cervical sponge from contamination both prior to and during insertion.

The outer tube 11 is generally of thin-walled construction having a smooth leading edge and smooth outer walls to facilitate its insertion into the vagina and to preclude any injury to the internal organs. Preferably, an inexpensive, sterilizable material such as rubber or suitable plastic having sufficient rigidity for use in the manner hereinafter explained is utilized. Polyethylene is a preferred thermoplastic material and is used throughout in the construction of this device with the exception of the cervical sponge 13 and the flexible mucous membrane 14. Polyethylene has the advantage of being sufficiently rigid, biologically compatible, easily sterilized, and can be readily extruded or molded by injection or compression. The dimensions of the outer tube are such in nature that insertion is readily achieved in the average woman without undue force or pressure.

Figure 2:
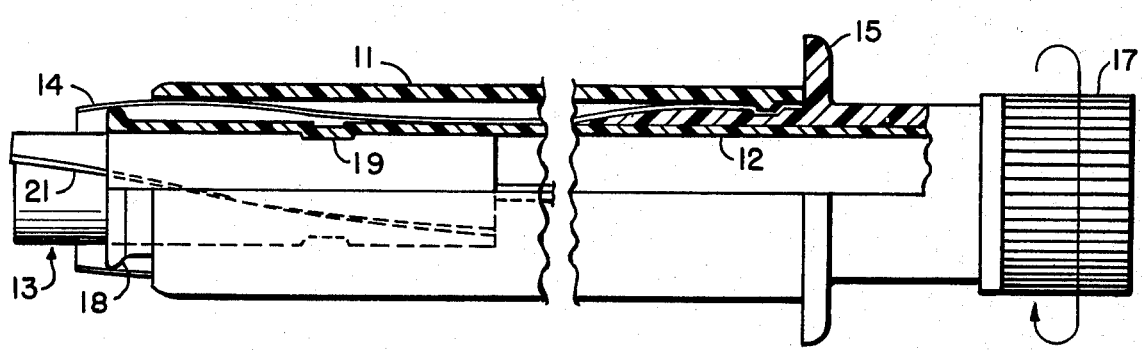
FIG. 2 is a cross-sectional view of the device with the cervical sponge having been extended through the mucuous-protecting sleeve.
Figure 3:
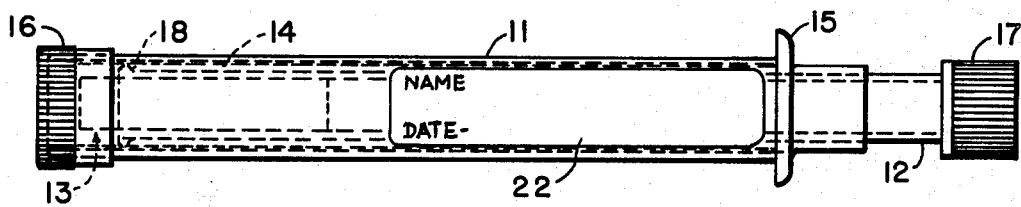
FIG. 3 is an elevational view of the device equipped with a mailing label.

The outer tube may vary from 1.0 to 2.0 cm. in its outside diameter and range from 10.0 to 15.0 cm. in length. Preferably, an outer tube of 12.7 cm. in length is employed, which is the standard gynecological distance to the cervical site of a mature woman. In a preferred embodiment of this invention, a cervical stop 15 is fitted at the rear of the outer tube as shown in FIG. 2 and FIG. 3. As can be seen, the cervical stop serves not only to position the forward end of the outer tube directly beneath and in front of the cervix, but also to act as a bushing for the inner tube to slide freely within the outer tube. The outer tube may also be equipped with a protective cap 16 as shown in FIGS. 1 and 3 so as to protect the cervical sponge from contamination and dehydration both prior and subsequent to use.

The inner tube 12 acts as a plunger within the outer tube. It is slightly longer than the outer tube and is arranged so as to be in a slidable telescopic relationship thereto. A finger-gripping portion of knob 17 can be fastened to the far end of the inner tube and serves to act as a stop when the inner tube is fully extended as indicated in FIG. 2. When properly inserted by the user, the forward end of the fully extended inner tube 12 containing the cervical sponge 13 is automatically in the position so as to obtain a tissue sample in the region of the squamo-columnar junction at the uterine cervix. The leading edge of the inner tube is smoothly curved or beaded to facilitate penetration and prevent internal injury from occurring.

A preferred embodiment of this invention includes a beaded or rolled rim 18 at the forward end of the inner tube as shown in FIG. 2. This rim 18 additionally serves as a guide, which in combination with the bushing effect of the cervical stop 15, permits the inner tube to slide and rotate freely within the outer tube without jamming or binding.

The cervical sponge 13 is mounted at the forward end of the inner tube in any convenient manner, such as by sonic welding, solvent fusion, or adhesive bonding. Preferably, the inner tube is crimped to the cervical sponge as indicated by 19 in FIG. 2, thereby avoiding the possibility of any sensitivity or allergenic reactions as a result of the additional chemical agents employed. The sponge material can be of any suitable character including nylon, polyurethane foam, cellulose or other synthetic surgical sponge material. The sponge should be lint-free, easily sterilized, and, of course, remain inert to the fixative solution employed.

Figure 4:
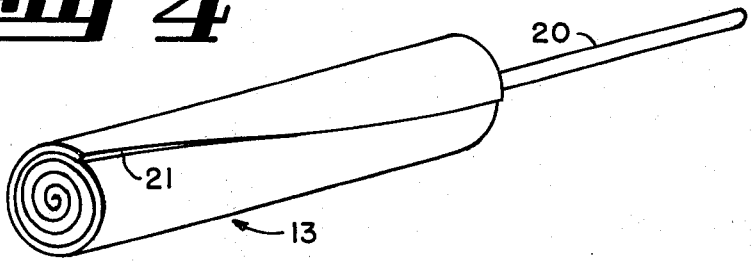
FIG. 4 is a perspective view of a preferred embodiment of the cervical sponge taken from one side at the forward end thereof.

The preferred sponge material for use herein comprises a high-purity, cellulose sponge cloth of fine porosity. In the dry state, the cellulose sponge is hard and abrasive. When moistened with water or aqueous solutions, however, the sponge becomes soft and at the same time compressible and expandable so as to exert a gentle wiping action at the cervix. FIG. 4 shows a preferred embodiment of the sponge in which the cellulose sponge cloth 13 is spirally wound on a polyethylene rod 20, as shown in FIG. 4. The leading edge of the sponge cloth 21 acts as a soft, flexible wiper which collects the cervical tissue cells so they may be absorbed and retained by the sponge. It is this gentle wiping action, as compared to the scraping action of the prior art, that provides a rich sampling of atypical cells when present, thereby increasing the probability for positive diagnoses.

In general, the sponge is pre-moistened with 1 to 2 cc. of a suitable fixative solution, although this can also be added just prior to use. Suitable fixative solutions comprise aqueous solutions of glycerine and the lower alkanols. The glycerine is present in amounts ranging from 1 to 2 percent by volume of the total volume of the fixative solution and is present to prevent the collected tissue cells from swelling or shrinking. Saline or physiological salts can also be added to achieve the same purpose. The term lower alkanol includes those aliphatic alcohols having from 1 to 4 carbon atoms, as for example, methanol, ethanol, propanol, isopropanol, butanol, isobutanol, and t-butanol. The alkanol concentration ranges from about 25 to 50 percent by volume of the total volume of the fixative solution and should be sufficiently high as to inhibit bacterial growth and/or decomposition of the tissue cell material collected. Alternatively, small amounts of fungicides or antibiotics can be added to the fixative solution to inhibit the decomposition of the cell sample on prolonged storage. A simple and preferred aqueous fixative solution comprises a solution of from about 1 to 2 percent of glycerine by volume and from about 20 to 40 percent of ethyl alcohol by volume.

The mucous-protecting sleeve 14 encloses the inner tube and sponge assembly as shown in FIG. 1. Once the cervical sponge has been sterilized, the mucous-protecting sleeve maintains sterility and prevents further contamination from occurring. It also serves to act as a vapor barrier preventing the pre-moistened sponge from drying. Most importantly, however, the mucous-protecting sleeve prevents contamination of the cervical sponge from the normal body fluids and vaginal secretions present upon insertion into the vagina, and permits a cervical tissue sample to be collected which is free from such contamination.

The film sleeve can be prepared from any film material that is thin enough to substantially retain its folded configuration. Preferably, a polyethylene film of 0.5 mil or less in thickness is utilized. A polycarbonate film may also be utilized in the present invention. Such polycarbonate films are thermoplastic linear polyesters of carbonic acid derived from the polymeric condensation of bisphenols with one or more phosgenes, as for example phosgene itself or its derivatives. Such films are commercially available under the Trademark, "Nucleopore" from the Nucleopore Corporation in Pleasanton, Calif. While the thickness of the film is not critical, a thickness of from about 8 to 13 microns is preferred, with a film thickness of 10 microns being especially favored.

In fabricating the sleeve, it may be extruded as a seamless tube, or it may be formed from a flat sheet rolled into a tube with overlapping or butt seams. The sleeve is fastened to the inner wall of the outer tube and may be attached to said tube by heat, sealing, heat-shrinking, suitable adhesives or by friction with the cervical stop as indicated in FIG. 2. The mucous-protecting sleeve is folded over the forward edge of the sponge in a manner as to become unfolded when the sponge is pushed therethrough during ejection as is illustrated in FIG. 2.

In operation, the cervical tissue cell-gathering device is assembled, sterilized and dispensed as a single unit, which may or may not have a mailing label as shown in FIG. 3. The cap 16 is removed, and the woman desiring to obtain her own cervical tissue cell specimen, inserts the outer tube assembly into the vaginal canal until stopped by the vaginal shield 15. Thus, properly positioned, the user extends the inner tube 12 containing the moistened cervical sponge 13 through the thin, flexible, mucous-protecting sleeve 14 by means of the finger-gripping portion of knob 17. This moves the cervical sponge forward and in contact with the posterior vaginal fornix. The knob 17 is fully rotated to sample the cervical tissue and collect these cells onto the cervical sponge. The inner tube 12 containing the cell-laden, cervical sponge 13 is withdrawn into the outer tube 11 by rearwardly pulling knob 17. The entire unit is then withdrawn from the vagina, the protective cap 16 attached, the mailing label 22 completed, if necessary, and the tube transported to a clinical laboratory for subsequent microscopic examination.

The distribution of the cellular material on a microscope slide is accomplished by removal of the protective cap 16 and extending the cervical sponge as far forward as it will go by means of knob 17. The sponge can then be placed on a clean microscope slide and compression-rolled over the slide, thereby depositing a uniform number of cells throughout the entire area of the slide.

It can be readily appreciated that the cervical tissue cell-gathering device described herein eliminates contamination of the cell preparation, inasmuch as the cell-gathering sponge is never touched by human hands. The cervical cellular material so obtained in evenly distributed throughout the surface of the sponge and the presence of the fixative solution in the sponge at the time the sample is collected assures an intimate contact of all of the cells with the fixative solution. Slides prepared in this fashion are rich in cervical tissue cells, are of uniform density and are free from vaginal secretions and exudates.

It can be seen that the device described hereinabove can also be particularly adapted to a wide variety of diagnostic purposes. First and foremost, however, it is especially suited for use in obtaining a cervical smear for diagnosis in a Pap test. With minor modifications, this device can also be used to collect pathological bacteria and fungi in order to diagnose troublesome infections in the vaginal tract itself. Additionally, this device lends itself to the application of ointments, liquid medications and predetermined dosages of antibiotic and antifungal agents for delivery to specific sites in the vagina, as for example the cervix and the anterior or posterior vaginal fornix.

While several embodiments of the inventive concept have been set forth herein, it is understood that the invention is not to be construed as limited thereby, and that suitable changes, modifications and variations may be made without departing from the spirit and scope of the invention as defined in the following claims.

We claim:
1. A cervical tissue cell-gathering device comprising:
   an outer tube;
   an inner tube, slightly longer than said outer tube, telescopically positioned within said outer tube and longitudinally movable therein;
   a moistened cervical sponge mounted at the forward end of and projecting from said inner tube, said sponge moistened with a fixative solution for preserving cervical tissue cells; and
   a thin, flexible, mucous-protecting sleeve which encloses said inner tube and said cervical sponge before and during insertion into the vagina, one end of said sleeve being fastened to the inner wall of said outer tube, and the other end of said sleeve being folded over the forward end of said sponge in such a manner as to permit said cervical sponge to be extended therethrough.

2. A cervical cell-gathering device as set forth in claim 1 wherein a cervical stop is affixed to said outer tube.

3. A cervical cell-gathering device as set forth in claim 1 wherein the fixative solution is an aqueous solution comprising from 1 to 2 percent of glycerine, and from 25 to 50 percent of a lower alkanol having from 1 to 4 carbon atoms.

4. A cervical cell-gathering device according to claim 1 wherein the fixative solution is an aqueous solution comprising from 1 to 2 percent of glycerine and from 20 to 40 percent of ethyl alcohol.

5. A cervical cell-gathering device according to claim 1 wherein the mucous-protecting sleeve is a polyethylene film.

6. A cervical cell-gathering device according to claim 1 wherein the cervical sponge consists of spirally-wound layers of cellulose cloth sponge.

* * * * *